United States Patent
Govari

(10) Patent No.: US 10,952,797 B2
(45) Date of Patent: Mar. 23, 2021

(54) TRACKING A RIGID TOOL IN A PATIENT BODY

(71) Applicant: Biosense Webster (israel) Ltd., Yokneam (IL)

(72) Inventor: Assaf Govari, Haifa (IL)

(73) Assignee: Biosense Webster (Israel) Ltd., Yokneam (IL)

( * ) Notice: Subject to any disclaimer, the term of this patent is extended or adjusted under 35 U.S.C. 154(b) by 260 days.

(21) Appl. No.: 15/859,969

(22) Filed: Jan. 2, 2018

(65) Prior Publication Data

US 2019/0201103 A1    Jul. 4, 2019

(51) Int. Cl.
| | |
|---|---|
| *A61B 34/20* | (2016.01) |
| *A61B 34/10* | (2016.01) |
| *A61B 17/24* | (2006.01) |
| *A61B 90/00* | (2016.01) |
| *A61B 17/00* | (2006.01) |
| *G16H 40/63* | (2018.01) |

(52) U.S. Cl.
CPC ............. *A61B 34/20* (2016.02); *A61B 17/24* (2013.01); *A61B 34/10* (2016.02); *G16H 40/63* (2018.01); *A61B 90/37* (2016.02); *A61B 2017/00199* (2013.01); *A61B 2034/2051* (2016.02); *A61B 2034/2072* (2016.02); *A61B 2090/3762* (2016.02)

(58) Field of Classification Search
CPC ...................................................... A61B 34/20
See application file for complete search history.

(56) References Cited

U.S. PATENT DOCUMENTS

| | | | |
|---|---|---|---|
| 5,391,199 A | 2/1995 | Ben-Haim | |
| 5,879,297 A * | 3/1999 | Haynor | A61B 5/06 128/899 |
| 6,129,668 A * | 10/2000 | Haynor | A61B 5/06 128/899 |
| 6,239,724 B1 | 5/2001 | Doron et al. | |
| 6,263,230 B1 * | 7/2001 | Haynor | A61B 5/062 128/899 |
| 6,332,089 B1 | 12/2001 | Acker et al. | |
| 6,484,118 B1 * | 11/2002 | Govari | A61B 5/06 702/150 |
| 6,618,612 B1 | 9/2003 | Acker et al. | |
| 6,690,963 B2 | 2/2004 | Ben-Haim et al. | |
| 9,445,745 B2 * | 9/2016 | Cohen | A61B 5/06 |

(Continued)

FOREIGN PATENT DOCUMENTS

WO      WO9605768      2/1996

OTHER PUBLICATIONS

European Search Report dated May 21, 2019 from corresponding European Patent Application No. 18275235.2.

*Primary Examiner* — Raymond L Nimox

(74) *Attorney, Agent, or Firm* — Frost Brown Todd LLC

(57) ABSTRACT

An apparatus includes a memory and a processor. The memory is configured to hold values indicative of known relative positions of multiple position sensors of a position tracking system that are coupled to a medical device. The processor is configured to receive one or more signals indicative of estimated positions of the position sensors, as measured by the position tracking system, and to initiate a responsive action in response to detecting a discrepancy between the known relative positions and the estimated positions.

10 Claims, 3 Drawing Sheets

(56) References Cited

U.S. PATENT DOCUMENTS

| | | | | |
|---|---|---|---|---|
| 9,521,961 | B2* | 12/2016 | Silverstein | A61B 5/042 |
| 2002/0065455 | A1* | 5/2002 | Ben-Haim | A61N 1/36564 |
| | | | | 600/407 |
| 2003/0120150 | A1 | 6/2003 | Govari | |
| 2004/0068178 | A1 | 4/2004 | Govari | |
| 2006/0015031 | A1* | 1/2006 | Kienzle, III | A61B 5/103 |
| | | | | 600/424 |
| 2009/0264741 | A1* | 10/2009 | Markowitz | A61B 5/044 |
| | | | | 600/424 |
| 2010/0082280 | A1* | 4/2010 | Schneider | A61B 5/06 |
| | | | | 702/94 |
| 2011/0251814 | A1* | 10/2011 | Bar-Tal | A61B 5/062 |
| | | | | 702/95 |
| 2012/0065481 | A1 | 3/2012 | Hunter et al. | |
| 2013/0303878 | A1* | 11/2013 | Nevo | A61B 5/062 |
| | | | | 600/409 |
| 2014/0187905 | A1* | 7/2014 | Olson | A61B 5/066 |
| | | | | 600/409 |
| 2014/0187915 | A1* | 7/2014 | Yaroshenko | A61B 5/062 |
| | | | | 600/424 |
| 2015/0305823 | A1* | 10/2015 | Claus | A61B 5/061 |
| | | | | 600/424 |
| 2017/0079553 | A1* | 3/2017 | Gliner | A61B 5/066 |
| 2018/0110567 | A1* | 4/2018 | Amit | A61B 34/20 |
| 2018/0280049 | A1* | 10/2018 | Algawi | A61B 17/32 |
| 2019/0059833 | A1* | 2/2019 | Govari | A61B 6/12 |

* cited by examiner

TRACKING A RIGID TOOL IN A PATIENT BODY

FIELD OF THE INVENTION

The present invention relates generally to medical devices, and particularly to methods and systems for tracking a medical device in a patient body.

BACKGROUND OF THE INVENTION

Various medical procedures involve inserting a tool into a cavity in the patient body. Techniques for tracking a medical device in a patient body are known in the art.

For example, U.S. Patent Application Publication 2012/0065481, issued as U.S. Pat. No. 8,467,853 on Jun. 18, 2013, describes an image guided catheter navigation system for navigating a region of a patient. The catheter includes an imaging device, a tracking device, a controller, and a display. The imaging device generates images of the region of the patient. The tracking device tracks the location of the catheter in the region of the patient. The controller superimposes an icon representing the catheter onto the images generated from the imaging device based upon the location of the catheter. The display displays the image of the region with the catheter superimposed onto the image at the current location of the catheter.

U.S. Patent Application Publication 2011/0251814, issued as U.S. Pat. No. 8,536,859 on Sep. 17, 2013, describes a method for tracking a position of an object. The method includes using a field sensor associated with the object to measure field strengths of magnetic fields generated by two or more field generators, in which a measurement of at least one of the field strengths is subject to a distortion.

SUMMARY OF THE INVENTION

An embodiment of the present invention that is described herein provides an apparatus including a memory and a processor. The memory is configured to hold values indicative of known relative positions of multiple position sensors of a position tracking system that are coupled to a medical device. The processor is configured to receive one or more signals indicative of estimated positions of the position sensors, as measured by the position tracking system, and to initiate a responsive action in response to detecting a discrepancy between the known relative positions and the estimated positions.

In some embodiments, the processor is configured to correct the detected discrepancy based on the values indicative of the known relative positions. In other embodiments, the processor is configured to alert a user to the detected discrepancy. In yet other embodiments, the processor is configured to calculate the estimated positions based on the received one or more signals.

In an embodiment, the processor is configured to compare between values of the known relative positions and values of the estimated positions so as to detect the discrepancy. In another embodiment, the known relative positions include known relative positions of first, second and third position sensors coupled to the medical device, and the received signals include signals indicative of estimated positions of the first, second and third position sensors. The processor is configured to: (i) detect one or more distorted measurements of the first position sensor, by detecting a discrepancy between a known relative position of the first position sensor and an estimated position of the first position sensor, and (ii) correct the discrepancy based on the received signals of the second and third position sensors, and on the known relative positions of the first, second and third position sensors. In yet another embodiment, the medical device includes an ear-nose-throat (ENT) tool, and the position sensors are coupled along a longitudinal axis of the ENT tool.

There is additionally provided, in accordance with an embodiment of the present invention, a method including holding values indicative of known relative positions of multiple position sensors of a position tracking system that are coupled to a medical device. One or more signals indicative of estimated positions of the position sensors, as measured by the position tracking system, are received. A responsive action is initiated in response to detecting a discrepancy between the known relative positions and the estimated positions.

The present invention will be more fully understood from the following detailed description of the embodiments thereof, taken together with the drawings in which:

DETAILED DESCRIPTION OF EMBODIMENTS

Overview

Some medical procedures, such as ear-nose-throat (ENT) procedures, require navigating a rigid ENT tool in a patient head.

In principle, the ENT tool may be tracked in the patient head by coupling a position sensor of a magnetic position tracking system to the distal end of the tool. The position measurements may be calibrated by applying a predefined magnetic field using the magnetic position tracking system and estimating the position of the position sensor. In some cases, however, the magnetic field applied (e.g., during the ENT procedure) by the position tracking system may be distorted, e.g., by metallic objects (e.g., additional tools) introduced during the ENT procedure. If the distortion caused to the magnetic field is not taken into consideration, it may degrade the tracking accuracy of the ENT tool in the patient head.

Embodiments of the present invention that are described hereinbelow provide improved techniques for tracking a rigid ENT tool in a patient head in the presence of distorted magnetic fields. In some embodiments, instead of using a single position sensor, multiple (e.g., three) position sensors of a magnetic position tracking system are coupled at known relative positions (e.g., along a longitudinal axis of the ENT tool) that are stored in a memory. Since the ENT tool is rigid, each of the position sensors has a fixed known position relative to the other position sensors.

In some embodiments, a processor is configured to receive signals indicative of estimated positions of the position sensors, as measured by the position tracking system, and to compare between the values of the known and the estimated relative positions. In some embodiments, the processor is configured to initiate a suitable action in response to detecting a discrepancy between the known and the estimated relative positions.

In some embodiments, the processor is configured to use the known relative positions among the multiple position sensors, so as to detect and correct one or more distorted measurements carried out by one or more of the position sensors.

The disclosed techniques enable improved quality of minimally-invasive medical procedures by allowing introduction of multiple ENT tools or other objects that may cause distortion to the magnetic field, without compromising the accuracy in tracking the positions of the involved tools.

Furthermore, the disclosed techniques enable real time adaptation to time-varying conditions and interference.

System Description

Figure 1:
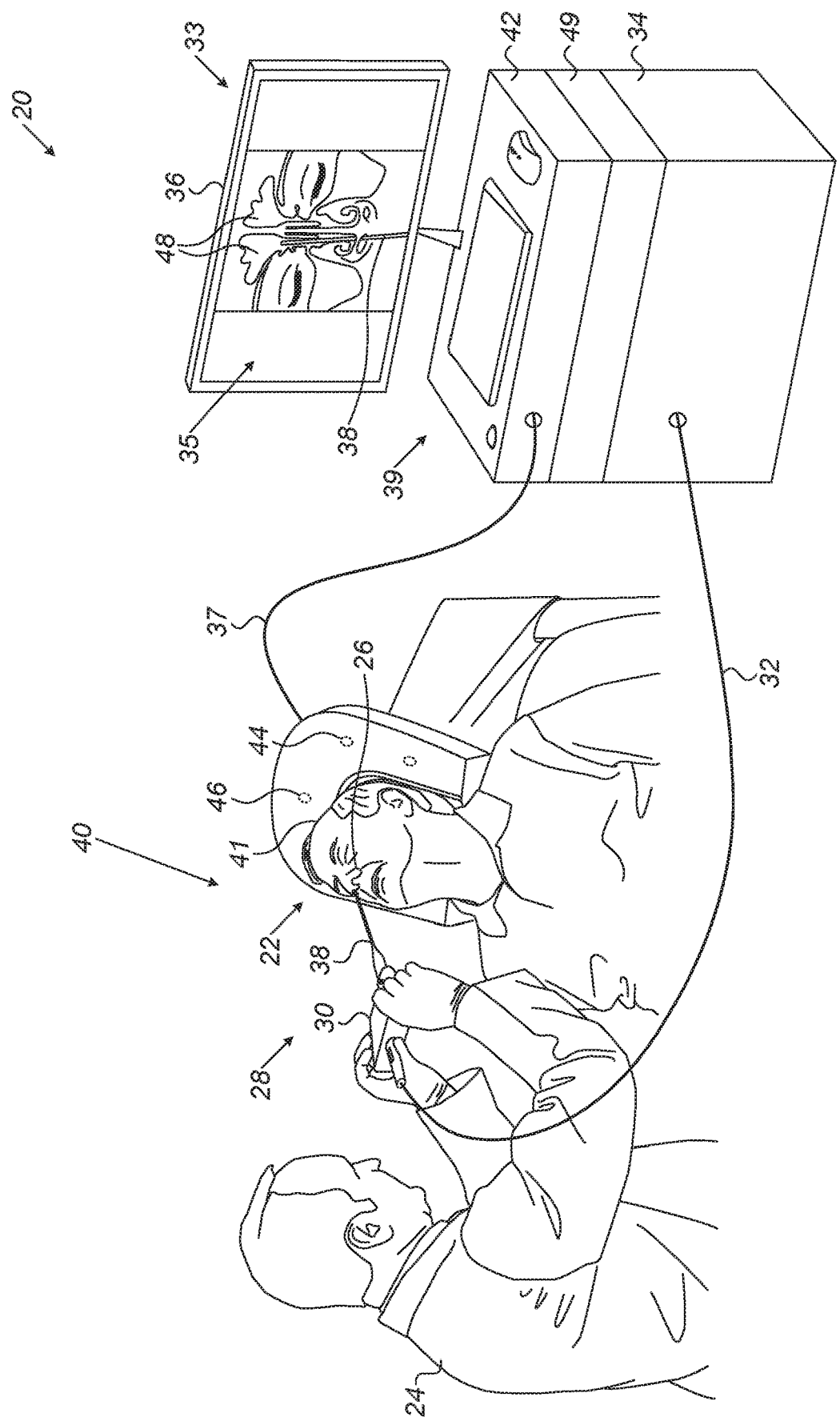
FIG. 1 is a schematic, pictorial illustration of an ear-nose-throat (ENT) procedure using an ENT system, in accordance with an embodiment of the present invention.

FIG. 1 is a schematic, pictorial illustration of an ear-nose-throat (ENT) procedure using an ENT system 20, in accordance with an embodiment of the present invention. In some embodiments, ENT system 20 comprises an ENT module 28, which is configured to carry out an ENT procedure, such as treating infection from one or more sinuses 48 of a patient 22.

In some embodiments, ENT module 28 comprises an ENT tool 38 coupled to the distal end, which a physician 24 inserts into a nose 26 of patient 22. Module 28 further comprises a handheld apparatus 30, coupled to a proximal end of ENT tool 38 and configured to assist physician 24 in navigating tool 38 in a head 41 of patient 22.

In some embodiments, apparatus 30 is further configured to apply suction, so as to remove the infection away from an infected sinus 48. ENT suction tool 38 is depicted in further detail in FIG. 2 below.

In an embodiment, system 20 further comprises a magnetic position tracking system, which is configured to track the position of one or more position sensors in head 41. The magnetic position tracking system comprises magnetic field-generators 44 and multiple position sensors shown in FIGS. 2A and 2B below. The position sensors generate position signals in response to sensing external magnetic fields generated by field generators 44, thereby enabling a processor 34 to estimate the position of each sensor as will be described below.

This method of position sensing is implemented in various medical applications, for example, in the CARTO™ system, produced by Biosense Webster Inc. (Irvine, Calif.) and is described in detail in U.S. Pat. Nos. 5,391,199, 6,690,963, 6,484,118, 6,239,724, 6,618,612 and 6,332,089, in PCT Patent Publication WO 96/05768, and in U.S. Patent Application Publications 2002/0065455 A1, issued as U.S. Pat. No. 6,690,963 on Feb. 10, 2004, 2003/0120150 A1, issued as U.S. Pat. No. 7,729,742 on Jun. 1, 2010, and 2004/0068178 A1, now abandoned, whose disclosures are all incorporated herein by reference.

System 20 further comprises a location pad 40, which comprises field-generators 44 fixed on a frame 46. In the exemplary configuration shown in FIG. 1, pad 40 comprises five field-generators 44, but may alternatively comprise any other suitable number of generators 44. Pad 40 further comprises a pillow (not shown) placed under head 41 of patient 22, such that generators 44 are located at fixed, known positions external to head 41.

In some embodiments, system 20 comprises a console 33, which comprises a memory 49, and a driver circuit 42 configured to drive, via a cable 37, field-generators 44 with suitable signals so as to generate magnetic fields in a predefined working volume in space around head 41.

In some embodiments, console 33 comprises a processor 34, typically a general-purpose computer, with suitable front end and interface circuits for receiving signals from tool 28 having multiple magnetic sensors coupled thereto (shown in FIG. 2 below), via a cable 32, and for controlling other components of system 20 described herein.

In some embodiments, processor 34 is configured to estimate the position of each position sensor. Based on the estimated positions of the sensors, processor 34 is configured to derive the position and orientation of the distal end of tool 28 (shown in FIG. 2 below) in the coordinate system of the magnetic position tracking system.

In some embodiments, processor 34 is configured to receive via an interface (not shown), one or more anatomical images, such as computerized tomography (CT) images depicting respective segmented two-dimensional (2D) slices of head 41, obtained using an external CT system (not shown). The term "segmented" refers to displaying various types of tissues identified in each slice by measuring respective attenuation of the tissues in the CT system.

Console 33 further comprises input devices 39 for controlling the operation of the console, and a user display 36, which is configured to display the data (e.g., images) received from processor 34 and/or to display inputs inserted by a user using input devices 39 (e.g., by physician 24).

In some embodiments, processor 34 is configured to select one or mode slices from among the CT images, such as an image 35, and to display the selected slice on user display 36. In the example of FIG. 1, image 35 depicts a sectional front-view of one or more sinuses 48 of patient 22.

FIG. 1 shows only elements related to the disclosed techniques, for the sake of simplicity and clarity. System 20 typically comprises additional modules and elements that are not directly related to the disclosed techniques, and thus, intentionally omitted from FIG. 1 and from the corresponding description.

Processor 34 may be programmed in software to carry out the functions that are used by the system, and to store data in memory 49 to be processed or otherwise used by the software. The software may be downloaded to the processor in electronic form, over a network, for example, or it may be provided on non-transitory tangible media, such as optical, magnetic or electronic memory media. Alternatively, some or all of the functions of processor 34 may be carried out by dedicated or programmable digital hardware components.

Tracking a Rigid ENT Tool in a Distorted Magnetic Field

Figure 2B:
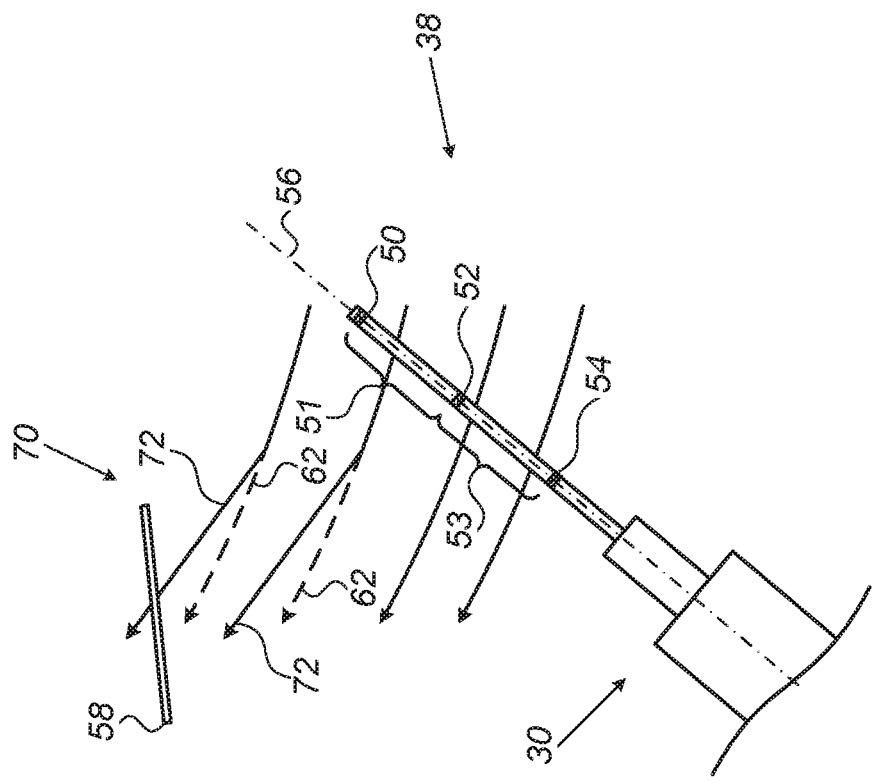
FIGS. 2A and 2B are schematic, pictorial illustrations of an ENT tool applied in an ENT procedure, in accordance with embodiments of the present invention.
Figure 2A:
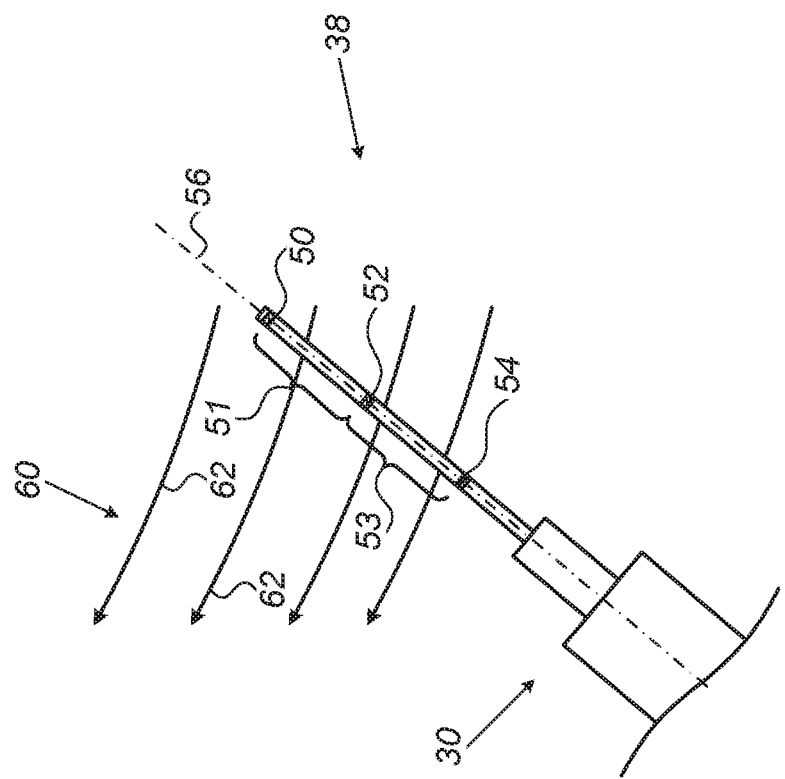

FIG. 2A is a schematic, pictorial illustration of ENT tool 38 applied, for example, in the ENT procedure depicted in FIG. 1 above, in accordance with an embodiment of the present invention. In some embodiments, ENT tool 38 comprises multiple position sensors, such as position sensors 50, 52 and 54, coupled at known relative suitable positions on ENT tool 38, for example, along a longitudinal axis 56 of ENT tool 38.

In the context of the present disclosure, the term "known relative positions" refers to the actual positions of sensors 50, 52 and 54, relative to one another, or relative to a predefined reference position on tool 38, or using any other suitable method. The actual relative positions of the position sensors are typically defined in the design of the tool and, during production, can be measured using any suitable measurement means.

In an embodiment, tool 38 may have a straight form, as shown for example in FIG. 2A. In this embodiment, the known relative position between sensors 50 and 52 may be defined by a distance 51 between these position sensors. Similarly, the known relative position between sensors 52 and 54 may be determined by a distance 53. In this example, the known relative position between sensors 50 and 54 is given by the summing distances 51 and 53.

In other embodiments, any other suitable definition and measurement may be applied to obtain the known relative positions. For example, in case the ENT tool has a curved shape or an irregular shape, the known relative positions between each pair of position sensors, coupled along the tool, may be determined in a form of a Euclidean vector having a magnitude (or length) and a direction.

In some embodiments, the known relative positions of sensors 50, 52 and 54 are stored in memory 49 of system 20. The known relative positions may be provided, for example, by the ENT tool manufacturer.

In some embodiments, during the ENT procedure, magnetic field-generators 44 apply a magnetic field 60 shown by magnetic field lines 62. As depicted in FIG. 1 above, processor 34 is configured to estimate the position of each of position sensors 50, 52 and 54 based on signals received from position sensors 50, 52 and 54 indicative of their respective positions in the coordinate system of the magnetic position tracking system.

In some embodiments, processor 34 is configured to calculate, based on the estimated positions, respective estimated relative positions of sensors 50, 52 and 54. The estimated relative positions may be defined, for example, as two distances: a first estimated distance between sensors 50 and 52, which corresponds to known distance 51, and a second estimated distance between sensors 52 and 54, which corresponds to known distance 53.

In some embodiments, processor 34 is configured to compare between the first estimated distance and known distance 51, and to compare between the second estimated distance and known distance 53.

In some embodiments, processor 34 stores (in memory 49 or in a memory of processor 34) a threshold value for determining whether a discrepancy exists between a given known distance and a corresponding estimated distance. The threshold value that determines the discrepancy may be different among at least two of the known distances, or alternatively, may be similar for all known distances.

In some embodiments, tool 38 is calibrated, typically before conducting the procedure, with respect to one or more predefined magnetic fields, so as to minimize the initial discrepancy levels.

FIG. 2B is a schematic, pictorial illustration of ENT tool 38 applied in an ENT procedure, in accordance with an embodiment of the present invention. In the example of FIG. 2B, physician navigates tool 38 is proximity to a metallic object 58, such as a metallic distal end of another medical device, or a metallic implantable device in head 41 of patient 22.

The presence of object 58, and in particular, the proximity between object 58 and the distal tip of tool 38, may cause a deflection of magnetic field lines 62 (shown in dashed lines in FIG. 2B) to form, instead, deflected magnetic field lines 72 of a distorted magnetic field 70.

Note that the deflection of the magnetic field lines occurs in field lines 72 traversing near position sensor 50, whereas the magnetic field lines traversing near sensors 52 and 54 are less affected by the distortion of the magnetic field.

In some embodiments, processor 34 is configured to detect a discrepancy above the predefined threshold between the values of the first estimated distance and known distance 51, whereas the values of the second estimated distance and known distance 53 will conform to one another (i.e., the discrepancy detected is below the predefined threshold).

In some embodiments, processor 34 may initiate a responsive action in response to detecting the discrepancy between the first estimated distance and known distance 51.

In an embodiment, in applying the responsive action, processor 34 may display an alert message to physician 24, e.g., on display 36, to hold the ENT procedure. In another embodiment, processor 34 is configured to detect one or more distorted position measurements carried out by at least one position sensor, e.g., sensor 50, by detecting a discrepancy between the known relative position of sensor (e.g., distance 51 from sensor 52), and the distorted position as measured by sensor 50 (e.g., the distance between the estimated positions of sensors 50 and 52.)

In some embodiments, processor 34 is configured to correct the distorted position measurements carried out by sensor 50, based on distances 51 and 53 that determine the known relative positions of sensors 50, 52 and 54, and on the measurements carried out by position sensors 52 and 54.

In some embodiments, after correcting the distorted position measurements of sensor 50, processor 34 display, e.g., on user display 36, a message indicating that the distorted position measurements have been corrected successfully so that physician 24 may proceed with the ENT procedure.

The configuration of system 20, and particularly of ENT tool 38 are depicted by way of example for the same of conceptual clarity. In other embodiments, any alternative configuration may be used, for example, the number of position sensors, and the distances between each couple of the position sensors may vary, so as to comply with various requirements, such as medical, regulatory, or technical requirements.

Figure 3:
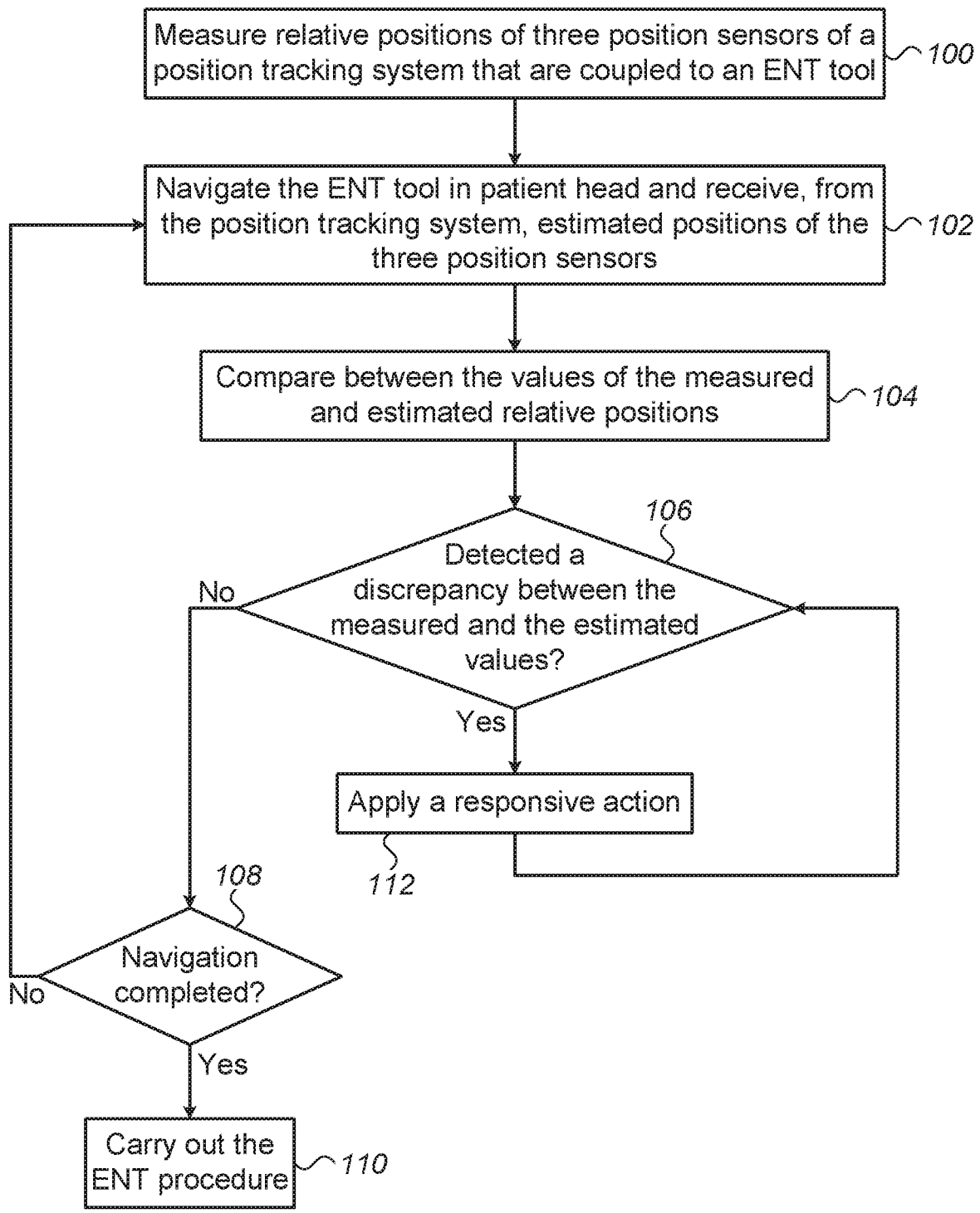
FIG. 3 is a flow chart that schematically illustrates a method for tracking an ENT tool in a patient body, in accordance with an embodiment of the present invention.

FIG. 3 is a flow chart that schematically illustrates a method for tracking ENT tool 38 in patient head 41, in accordance with an embodiment of the present invention. The method begins at a measurement step 100, in which before conducting the ENT procedure, a technician, for example, measures along ENT tool 38, relative positions of position sensors 50, 52 and 54, such as distances 51 and 53 depicted in FIG. 2A above. In some embodiments, the technician or another user stores distances 51 and 53 in memory 49 of console 33.

At a tool navigation step 102, physician 24 inserts ENT tool 38 into patient head 41 and receives from processor 34, based on signal measured by the position tracking system, the estimated positions of sensors 50, 52 and 54. In some embodiments, processor 34 calculates, based on the estimated positions, the first estimated relative distance between sensors 50 and 52, and the second estimated relative distance between sensors 52 and 54.

At a comparison step 104, processor 34 compares between the calculated values of the relative distances and the corresponding estimated positions. For example, processor 34 compares between the values of the first estimated distance and known distance 51, so as to detect whether there is a discrepancy (e.g., above the predefined threshold) related to the relative positions of sensors 50 and 52. Processor may repeat the comparison between other values, such as between the second estimated distance and known distance 53, so as to detect whether there is a discrepancy related to the relative positions of sensors 52 and 54.

In other embodiments, processor 34 may compare between the measured relative positions and the estimated relative positions of sensors 50, 52 and 54 using any other suitable technique, rather than comparing between the known and estimated relative distances.

At a discrepancy detection step 106, processor 34 checks whether there is a discrepancy between any of the measured (i.e., known) relative position values stored in memory 49, and the estimated relative position values obtained based on the positions of sensors 50, 52 and 54 measured by the position tracking system.

In case no discrepancy detected, the method proceeds to a navigation completion step 108, in which processor 34 or physician 24 checks whether ENT tool 38 is positioned at the target location in head 41, so that physician 24 may apply tool 38 to carry out the ENT procedure.

In case discrepancy was detected, the method is routed to a responsive action step 112, in which processor 34 notifies physician 24 of the detected discrepancy and, optionally, conducts one or more corrective actions, such as correcting the distorted position measurements carried out by sensor 50, as described in FIG. 2B above.

In other embodiments, processor 34 may recommend to the user by displaying a suitable message, and/or physician 24 may decide on terminating the procedure and retracting tool 38 out of the body of patient 22, as part of the responsive actions conducted in step 112.

In case processor 34 corrected the distorted position measurements carried out by sensor 50, the method loops back to detection step 106, in which processor 34 checks whether all the discrepancies detected in step 106 are corrected, e.g., are now below the predefined threshold.

In case all the discrepancies are corrected, the method is routed to navigation completion step 108 so as to check whether ENT tool is positioned at the target location, or whether the method loops back to navigation step 102.

In case the navigation is completed, the method is routed to an ENT procedure step 110, which terminates the method. At step 110, ENT tool is positioned at the target location in head 41 (e.g., sinus 48) and physician 24 may carry out the ENT procedure, such as applying ENT tool 38 for suctioning infection from the infected sinus 48.

Although the embodiments described herein mainly address ENT procedures, the methods and systems described herein can also be used in other applications, such as in otolaryngology, cardiology or neurology.

It will thus be appreciated that the embodiments described above are cited by way of example, and that the present invention is not limited to what has been particularly shown and described hereinabove. Rather, the scope of the present invention includes both combinations and sub-combinations of the various features described hereinabove, as well as variations and modifications thereof which would occur to persons skilled in the art upon reading the foregoing description and which are not disclosed in the prior art. Documents incorporated by reference in the present patent application are to be considered an integral part of the application except that to the extent any terms are defined in these incorporated documents in a manner that conflicts with the definitions made explicitly or implicitly in the present specification, only the definitions in the present specification should be considered.

What is claimed is:

1. An apparatus, comprising:
    (a) a memory, which is configured to hold values indicative of known relative positions of multiple position sensors of a position tracking system that are coupled to a medical device; and
    (b) a processor, which is configured to:
        (i) receive one or more signals indicative of estimated positions of the position sensors, as measured by the position tracking system,
        (ii) initiate a responsive action in response to detecting a discrepancy between the known relative positions and the estimated positions, and
        (iii) when initiating the responsive action:
            (A) alert a user to the detected discrepancy,
            (B) correct the detected discrepancy based on the values indicative of the known relative positions, and
            (C) alert the user after the detected discrepancy is corrected.

2. The apparatus according to claim 1, wherein the processor is configured to calculate the estimated positions based on the received one or more signals.

3. The apparatus according to claim 1, wherein the processor is configured to compare between values of the known relative positions and values of the estimated positions so as to detect the discrepancy.

4. An apparatus, comprising:
    (a) a memory, which is configured to hold values indicative of known relative positions of multiple position sensors of a position tracking system that are coupled to a medical device; and
    (b) a processor, which is configured to receive one or more signals indicative of estimated positions of the position sensors, as measured by the position tracking system, and to initiate a responsive action in response to detecting a discrepancy between the known relative positions and the estimated positions,
    wherein the known relative positions comprise known relative positions of first, second and third position sensors coupled to the medical device, and the received signals comprise signals indicative of estimated positions of the first, second and third position sensors, and wherein the processor is configured to:
        (i) detect one or more distorted measurements of the first position sensor, by detecting a discrepancy between a known relative position of the first position sensor and an estimated position of the first position sensor; and
        (ii) correct the discrepancy based on the received signals of the second and third position sensors, and on the known relative positions of the first, second and third position sensors.

5. The apparatus according to claim 1, wherein the medical device comprises an ear-nose-throat (ENT) tool, and wherein the position sensors are each coupled to the ENT tool so that they are positioned on a shared axis that is parallel to a longitudinal axis of the ENT tool.

6. A method, comprising:
    (a) holding values indicative of known relative positions of multiple position sensors of a position tracking system that are coupled to a medical device;
    (b) receiving one or more signals indicative of estimated positions of the position sensors, as measured by the position tracking system; and
    (c) initiating a responsive action in response to detecting a discrepancy between the known relative positions and the estimated positions, wherein initiating the responsive action comprises:

(i) alerting a user to the detected discrepancy,
(ii) correcting the detected discrepancy based on the values indicative of the known relative positions, and
(iii) alerting the user after the detected discrepancy is corrected.

7. The method according to claim 6, further comprising calculating the estimated positions based on the received one or more signals.

8. The method according to claim 6, wherein detecting the discrepancy comprises comparing between values of the known relative positions and values of the estimated positions.

9. A method, comprising:
(a) holding values indicative of known relative positions of multiple position sensors of a position tracking system that are coupled to a medical device;
(b) receiving one or more signals indicative of estimated positions of the position sensors, as measured by the position tracking system; and
(c) initiating a responsive action in response to detecting a discrepancy between the known relative positions and the estimated positions,
wherein the known relative positions comprise known relative positions of first, second and third position sensors coupled to the medical device, and the received signals comprise signals indicative of estimated positions of the first, second and third position sensors, and wherein detecting the discrepancy comprises:
(i) detecting one or more distorted measurements of the first position sensor, by detecting a discrepancy between a known relative position of the first position sensor and an estimated position of the first position sensor; and
(ii) correcting the discrepancy based on the received signals of the second and third position sensors, and on the known relative positions of the first, second and third position sensors.

10. The method according to claim 6, wherein the medical device comprises an ear-nose-throat (ENT) tool, and wherein the position sensors are each coupled to the ENT tool so that they are positioned on a shared axis that is parallel to a longitudinal axis of the ENT tool.

* * * * *